United States Patent [19]
Dumoulin et al.

[11] Patent Number: 5,626,137
[45] Date of Patent: May 6, 1997

[54] APPARATUS AND METHODS FOR MAGNETIC RESONANCE (MR) ANGIOGRAPHY USING FLUIDS POLARIZED AT LOW TEMPERATURES

[75] Inventors: Charles L. Dumoulin, Ballston Lake, N.Y.; Steven P. Souza, Williamstown, Mass.; Robert D. Darrow, Scotia, N.Y.

[73] Assignee: General Electric Company, Schenectady, N.Y.

[21] Appl. No.: 537,572

[22] Filed: Oct. 2, 1995

[51] Int. Cl.⁶ ..................................................... A61B 5/055
[52] U.S. Cl. ..................................... 128/653.2; 128/653.3
[58] Field of Search ........................... 128/653.2, 653.3, 128/DIG. 27; 606/20

[56] References Cited

U.S. PATENT DOCUMENTS

| | | |
|---|---|---|
| 4,642,206 | 2/1987 | Honig . |
| 5,479,925 | 1/1996 | Dumoulin et al. . |
| 5,545,396 | 8/1996 | Albert et al. . |

Primary Examiner—Marvin M Lateef
Assistant Examiner—Shawna J. Shaw
Attorney, Agent, or Firm—Lawrence P. Zale; Marvin Snyder

[57] ABSTRACT

A magnetic resonance (MR) active invasive device system employs a small, high-field polarizing magnet, and a large, possibly low-field magnetic resonance (MR) imaging magnet for the purpose of generating MR angiograms of selected blood vessels. A subject is positioned in a large MR imaging magnet. A catheter is inserted into the patient at or near the root of a vessel tree to be imaged. A fluid, intended to be used as a contrast agent is first cooled and frozen, and then passed through the small high-field polarizing magnet where it becomes highly polarized. The frozen fluid is then heated and melted to physiologic temperatures and introduced into the subject through the catheter. Radiofrequency (RF) pulses and magnetic field gradients are then applied to the patient as in conventional MR imaging. Since the fluid has a larger longitudinal magnetization than tissue which has not passed through the polarizing magnet, the fluid produces a much larger MR response signal than other tissue, resulting in vessel tree images with excellent contrast.

7 Claims, 3 Drawing Sheets

APPARATUS AND METHODS FOR MAGNETIC RESONANCE (MR) ANGIOGRAPHY USING FLUIDS POLARIZED AT LOW TEMPERATURES

CROSS REFERENCES TO RELATED APPLICATIONS

This application is related to U.S. Patent applications "MAGNETIC RESONANCE (MR) ANGIOGRAPHY IN A LOW-FIELD IMAGING MAGNET" by C. Dumoulin, R. Darrow Ser. No. 08/264,283, filed Jun. 23, 1994, "MAGNETIC RESONANCE (MR) ANGIOGRAPHY USING A TOROIDAL POLARIZING MAGNET AND A LOW-FIELD IMAGING MAGNET" by C. Dumoulin and R. Darrow, Ser. No. 08/534,998, filed Sep. 27, 1995, now U.S. Pat. No. 5,609,153, issued Mar. 11, 1997; "MAGNETIC RESONANCE (MR) ANGIOGRAPHY USING AN INTEGRATED POLARIZING AND IMAGING MAGNET" by C. Dumoulin and S. Souza, Ser. No. 08/537,573, filed Oct. 2, 1995 now U.S. Pat. No. 5,603,320, issued Feb. 18, 1997; "APPARATUS AND METHODS FOR MAGNETIC RESONANCE (MR) ANGIOGRAPHY USING HYDROGEN POLARIZED AT LOW TEMPERATURES" by S. Souza and C. Dumoulin, Ser. No. 08/537,571, filed Oct. 2, 1995, now U.S. Pat. No. 5,611,340, issued Mar. 18, 1997, "APPARATUS AND METHODS FOR MAGNETIC RESONANCE (MR) IMAGING OF CAVITIES USING FLUIDS POLARIZED AT LOW TEMPERATURES" by S. Souza, C. Dumoulin, R. Darrow and H. Cline, Ser. No. 08/537,574, filed Oct. 2, 1995; and "MAGNETIC RESONANCE (MR) PERFUSION IMAGING IN A LOW-FIELD IMAGING MAGNET" by C. Dumoulin and S. Souza, Ser. No. 08/537,575, filed Oct. 2, 1995; all assigned to the present assignee, and all incorporated by reference.

BACKGROUND OF THE INVENTION

1. Field of the Invention

The present invention relates to medical imaging of blood vessels, and more particularly concerns the use of magnetic resonance to obtain such images.

2. Description of Related Art

Angiography, or the imaging of vascular structures, is very useful in diagnostic and therapeutic medical procedures. MR angiography is performed with a variety of methods, all of which rely on one of two basic phenomena. The first phenomenon arises from changes in longitudinal spin magnetization as blood moves from one region of the patient to another. Methods that make use of this phenomenon have become known as "in-flow" or "time-of-flight" methods. A commonly used time-of-flight method is three-dimensional time-of-flight angiography. With this method, a region of interest is imaged with a relatively short repetition time, TR, and a relatively strong excitation radio-frequency (RF) pulse. This causes the MR spins within the field-of-view to become saturated and give weak MR response signals. Blood flowing into the field-of-view, however, enters in a fully relaxed state. Consequently, this blood gives a relatively strong MR response signal, until it too becomes saturated. Because of the nature of blood vessel detection with time-of-flight methods, the stationary tissue surrounding the vessel cannot be completely suppressed. In addition, slowly moving blood, and blood that has been in the imaged volume for too long, becomes saturated and is poorly imaged.

A second type of MR angiography is based on the induction of phase shifts in transverse spin magnetization. These phase shifts are directly proportional to velocity and are induced by flow-encoding magnetic field gradient pulses. Phase-sensitive MR angiography methods exploit these phase shifts to create images in which the pixel intensity is a function of blood velocity. While phase-sensitive MR angiography can easily detect slow flow in complicated vessel geometries, it will also detect any moving tissue within the field-of-view. Consequently, phase-sensitive MR angiograms of the heart have artifacts arising from the moving heart muscle and from the moving pools of blood in the heart chambers.

In conventional MR imaging, an inhomogeneity of the static magnetic field produced by the main magnet causes distortion in the image. Therefore a main magnet having homogeneity over a large region is desirable.

Also, a stronger static magnetic field created by the main magnet, yields a better the signal to noise ratio, all other factors being equal. Typically, the magnets used to create the static magnetic field in an MR scanner have been constructed of a superconducting material requiring very low temperatures, and related support apparatus. These magnets can be very expensive.

Even if a very high field magnet were constructed to maximize the signal-to-noise ratio for MR angiographic imaging, the signal of the surrounding tissue would be increased to the same extent as signals from blood. Consequently, there would be no increase in vessel visibility with the higher magnetic field (assuming all other factors are equal).

Currently, there is a need for a system for obtaining high quality angiography of a selected vessel without the problems incurred with a large high-field imaging magnet.

SUMMARY OF THE INVENTION

A substance in the liquid state is passed through a polarizing means before it is injected into a catheter inserted in a vessel of a patient. The polarization means includes a high field magnet in which the substance is placed. The substance is made to reside in the polarizing magnetic field for a period longer than several times the longitudinal relaxation time, T1, of the substance. Additional polarization is obtained by lowering the temperature of the substance to form a frozen solid. After the solid has become highly polarized, it is removed from the polarizing magnet and rapidly heated to physiologic temperatures to result in a highly-polarized fluid. This polarized fluid is then injected into the patient. MR images are created of the polarized fluid with an MR system which is comprised of radio-frequency and magnetic field gradient coils and a static field imaging magnet. Since the strength of the detected MR signal is determined by the degree of polarization of the injected fluid, and not the strength of the imaging magnet, low-field resistive or permanent imaging magnets may be advantageously used instead of a higher field superconducting magnet.

OBJECTS OF THE INVENTION

It is an object of the present invention to provide a system for imaging selected blood vessels using magnetic resonance without the need for a homogeneous high-field imaging magnet.

It is another object of the present invention to provide a polarization means which can create highly polarized states in selected samples.

It is another object of the present invention to provide a means for the delivery of a highly polarized sample into a patient.

BRIEF DESCRIPTION OF THE DRAWINGS

The features of the invention believed to be novel are set forth with particularity in the appended claims. The invention itself, however, both as to organization and method of operation, together with further objects and advantages thereof, may be best understood by reference to the following description taken in conjunction with the accompanying drawing in which:

DETAILED DESCRIPTION OF THE INVENTION

Figure 1:
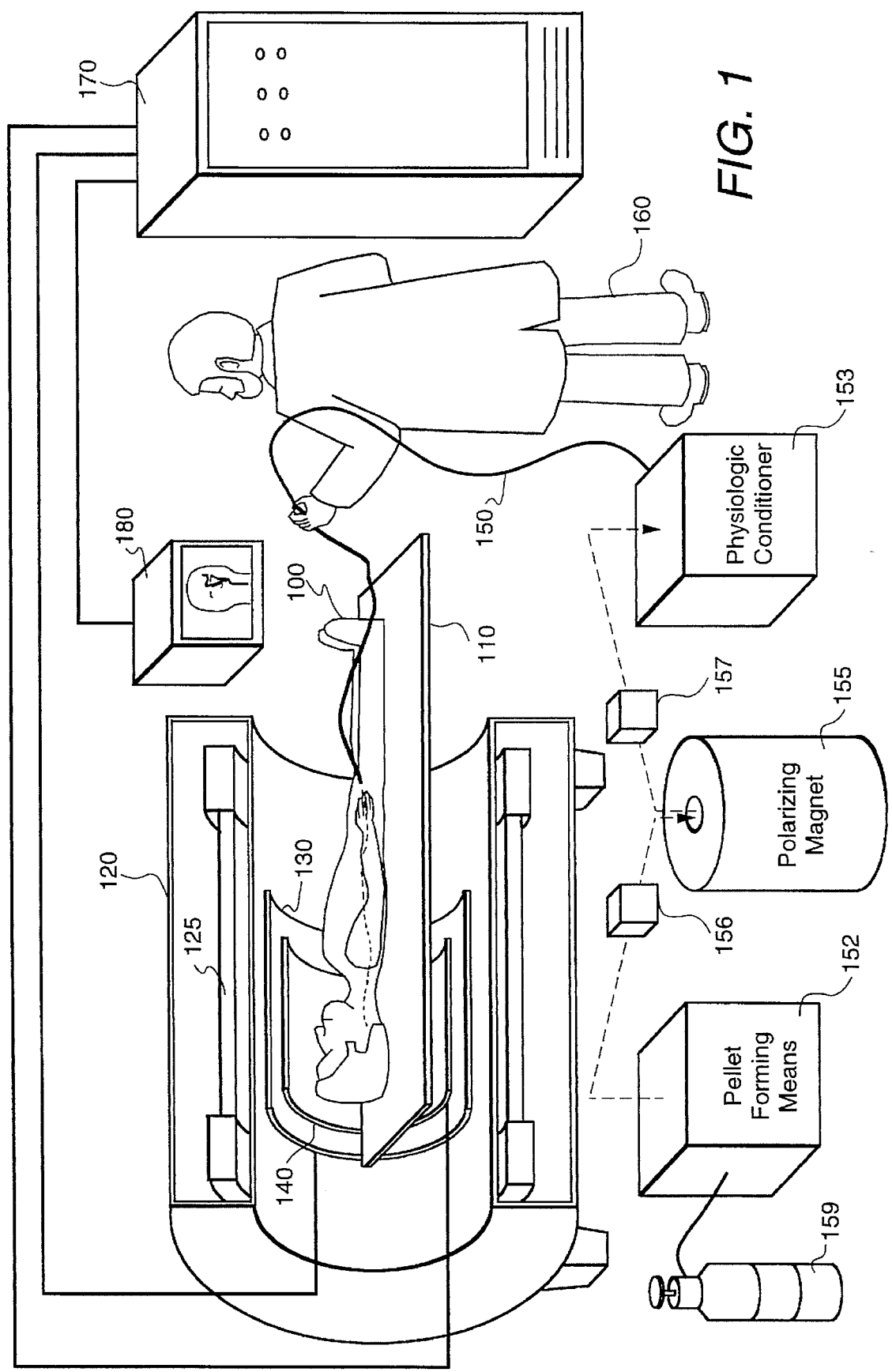
FIG. 1 is a perspective view of a first embodiment of the present invention in operation in which a vessel selective angiogram is being obtained from a subject.

In FIG. 1, a subject 100 is placed on a support table 110 and s positioned in a homogeneous magnetic field generated by a magnet 125 encased in a magnet housing 120. In this embodiment, magnet 125 and magnet housing 120 have cylindrical symmetry and are shown sectioned in half to reveal the position of subject 100. A region of interest of subject 100 is located in the approximate center of the bore of magnet 125. Subject 100 is surrounded by a set of cylindrical magnetic field gradient coils 130 which create magnetic field gradients of predetermined strength at predetermined times according to predetermined MR pulse sequences, described later. Gradient is coils 130 are capable of generating pulsed magnetic field gradients in three mutually orthogonal directions. At least one radio-frequency (RF) coil 140 (only one is shown in FIG. 1) also surrounds the region of interest of subject 100. In FIG. 1, RF coil 140 has a cylindrical shape with a diameter sufficient to encompass the entire subject. Other geometries, such as smaller cylinders specifically designed for imaging the head or an extremity, can be used in alternative embodiments. Non-cylindrical RF coils, such as surface coils, may also be used. RF coil 140 radiates radio-frequency energy into subject 100 at predetermined times and with sufficient power at a predetermined frequency so as to nutate a population of nuclear magnetic spins, hereinafter referred to as 'spins', of subject 100 in a fashion well known to those skilled in the art. RF coil 140 can also act as a receiver, detecting the MR response signals which are stimulated by nutation, if desired.

The nutation of the spins causes the spins to resonate at the Larmor frequency. The Larmor frequency for each spin is directly proportional to the strength of the magnetic field experienced by the spin. This field strength is the sum of the static magnetic field generated by magnet 125 and the local field generated by magnetic field gradient coil 130.

A selected fluid suitable for injection into subject 100 is first passed to through a cryogenic pellet forming means 152 which converts the selected fluid into frozen pellets. These pellets are then transferred to a polarizing magnet 155 where they become highly polarized. The pellets can be transferred to polarizing magnet 155 by an automated mechanical means 156, or manually in an insulated container.

Polarizing magnet 155 is a superconducting magnet operating with relatively poor homogeneity, but as high a field as practical. Designs in which the field strength reaches 15 Tesla or more are possible. If desired, the magnet can be substantially shielded to prevent stray magnetic fields from disturbing the surrounding environment. This shielding can be accomplished with an active cancellation coil surrounding the internal main coil. Since polarizing magnet 155 is not required to be highly homogeneous, and because of its small size, the magnet should be considerably less expensive than existing MR imaging magnets.

Once the pellets become highly polarized, they are removed from polarizing magnet 155 and put into a physiologic conditioner 153 where the pellets are rapidly melted and brought to approximately body temperature to give a highly polarized fluid. Transfer of the polarized pellets can be performed with a second automated mechanical means 157 or manually.

The highly polarized fluid is then injected through an invasive device 150, such as a catheter into subject 100 where it is imaged using conventional MR imaging methods.

The fluid which is injected into the subject 100 through catheter 150 should have the highest amount of polarization possible once it reaches the vessels. Consequently, the polarizing field of polarizing magnet 155 should be high. Also, the frozen fluid will have to be left in the polarizing field for a period of time greater than five times the T1 of the fluid to reach full magnetization. Once the frozen fluid is removed from polarizing magnet 155 it will begin to lose polarization with a time constant of T1. Since the T1 of the frozen fluid is likely to be long, it may be possible to move the frozen fluid relatively slowly, or even place it in storage for a selected time. As the fluid approaches room temperature, however, the T1 will shorten and transfer of the polarized fluid to physiological conditioner 153 and then through catheter 150 to subject 100 should be as rapid as possible.

In the current invention additional polarization is obtained by lowering the temperature of the pellets. The amount of additional polarization (and hence MR signal) can be derived from the Boltzmann equation:

$$n_e/n_0 = \exp\{-(E_e - E_0)/kT\} \quad (1)$$

where $n_e$ is the number of spins in the excited state, $n_0$ is the number of spins in the ground state, $E_e$ is the energy of the excited state, $E_0$ is the energy of the ground state, k is Boltzmann's constant and T is the temperature of the spins. It is useful to note that as the static magnetic field is increased, the energy of the excited state, $E_e$, increases. This results in a decrease in the ratio of the number of spins in the excited state, $n_e$, with respect to the number of spins in the ground state, $n_0$. Since the polarization of an ensemble of spins is directly proportional to the difference in the number of spins in the excited and ground states, stronger static magnetic fields give greater polarization and consequently, are often desirable. It is also useful to note in equation (1) that as the temperature, T, is lowered, the polarization of the spins increases. Consequently, an ensemble of spins which are polarized at low temperature attain a stronger degree of polarization.

Since it is the difference in the number of spins in the ground and excited states which determine the strength of the MR signal, S, it is useful to reformulate equation (1) such that:

$$S = C(n_0 - n_e) \quad (2)$$

and $$S = C\{n_0\{1 - \exp\{-(E_e - E_0)/kT\}\}\} \quad (3)$$

where C is a constant of proportionality.

Equation 3 can be used to calculate the change in signal intensity expected as the temperature, T, of the spins is changed. For example, if the temperature of the spins is lowered from room temperature to four degrees, Kelvin, Eq. (3) predicts a 66.5 fold increase in signal.

Figure 2:
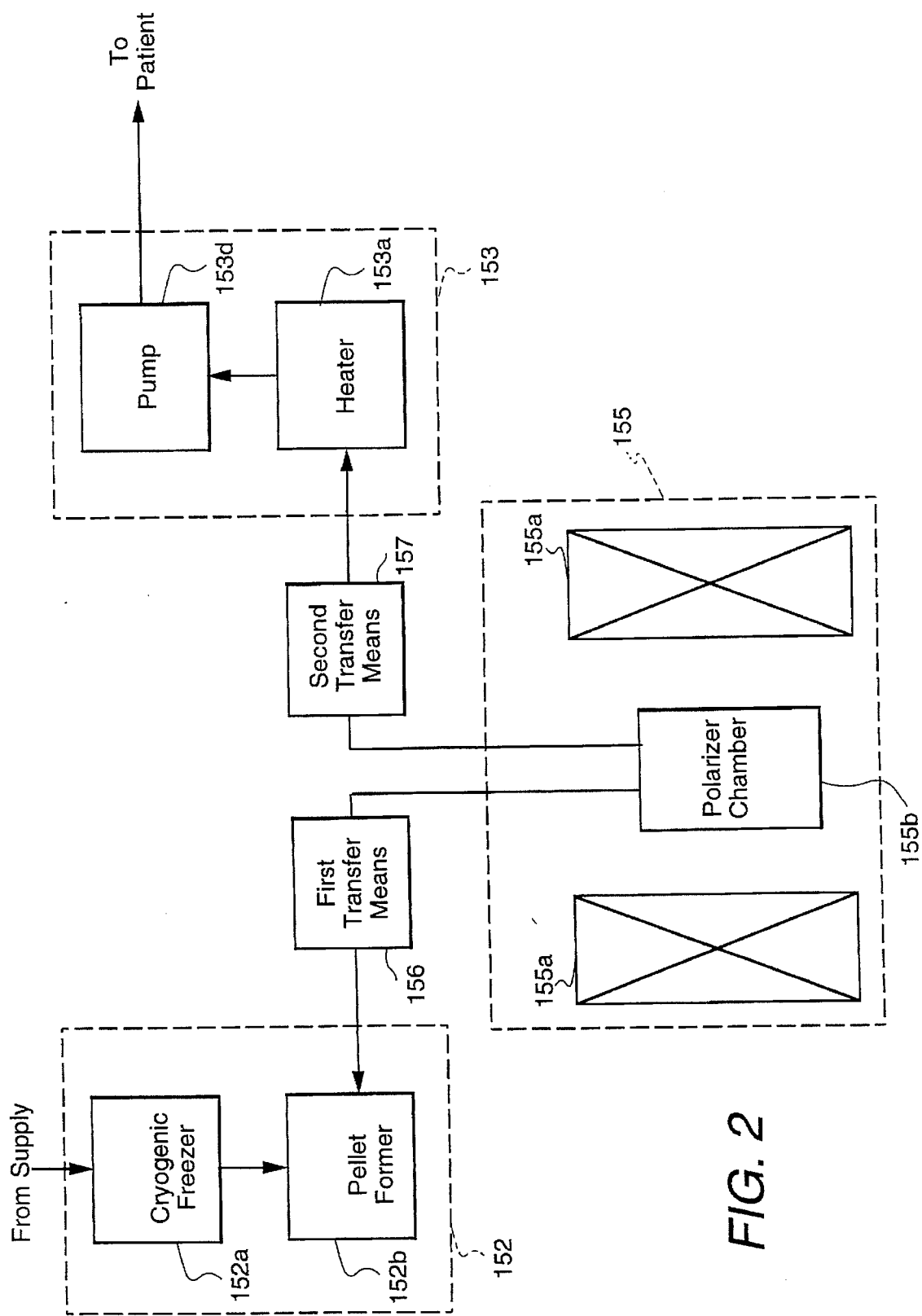
FIG. 2 is a schematic view of one embodiment of the present invention in which a liquid material is frozen, polarized and then prepared for injection into the subject.

FIG. 2 is a schematic diagram illustrating the components needed to produce highly polarized fluid suitable for injection into subject 100. Non-polarized fluid from a supply (159 of FIG. 1) is first introduced into cryogenic pellet forming means 152. Cryogenic pellet forming means 152 is comprised of a freezer portion 152a and a pellet former 152b. The net effect of cryogenic pellet forming means 152 is to convert the non-polarized fluid into a non-polarized solid at low temperature.

The non-polarized solid is then transferred to a polarizing magnet 155 where it is allowed to polarize. The solid approaches full polarization in an exponential hshion and polarization in excess of 99% of the maximum value can be achieved by allowing the solid to be in polarizing magnet 155 longer than five times the T1 of the solid. It should be noted that the T1 of the solid is likely to be relatively long at low temperatures.

After the solid has reached the desired level of polarization, the solid is removed from polarizing magnet 155 and placed into a physiologic conditioner 153. Physiologic conditioner 153 includes a heater 153a which rapidly raises the temperature of the highly-polarized solid to provide a highly-polarized liquid which is physiologically compatible with subject 100. The highly-polarized liquid is sent to catheter 150 via a pump 153b.

The current invention discloses the formation of pellets, but other embodiments in which the fluid is frozen into a rod shape, the rod is extruded, and then passed through polarizing magnet 155 on its way to physiologic conditioner 153 are possible. Other embodiments in which cryogenic pellet forming means 152, polarizing magnet 155 and physiologic conditioner 153 are combined into a single apparatus are also possible.

Once the fluid leaves polarizing magnet 155 it will begin to lose polarization with a time constant equal to its T1. Consequently, it is desirable to deliver the fluid to the patient as quickly as possible. This can be done by minimizing the length of catheter 150 and maximizing the flow velocity.

The fluid used for injection with the present invention should have a T1 chosen to be as long as possible to maximize the amount of polarization delivered into the vessels of the patient. Possible choices of fluid are:

1) physiological saline solution;
2) blood plasma; and
3) a blood substitute such as fluorinated hydrocarbons capable of carrying oxygen to tissue.

The imaging system will have many of the same elements as s a conventional MR imaging system. A static magnetic field from a main imaging magnet, shown as 125 in FIGS. 1, 3, may be relatively low (such as 0.1 Tesla) to reduce signals from "stationary" tissue and undesired blood pools contributing to the angiographic image. A small high-field polarization magnet 155 and a large low-field main magnet, instead of a large high-field main magnet, may reduce the cost of the system.

Figure 3:
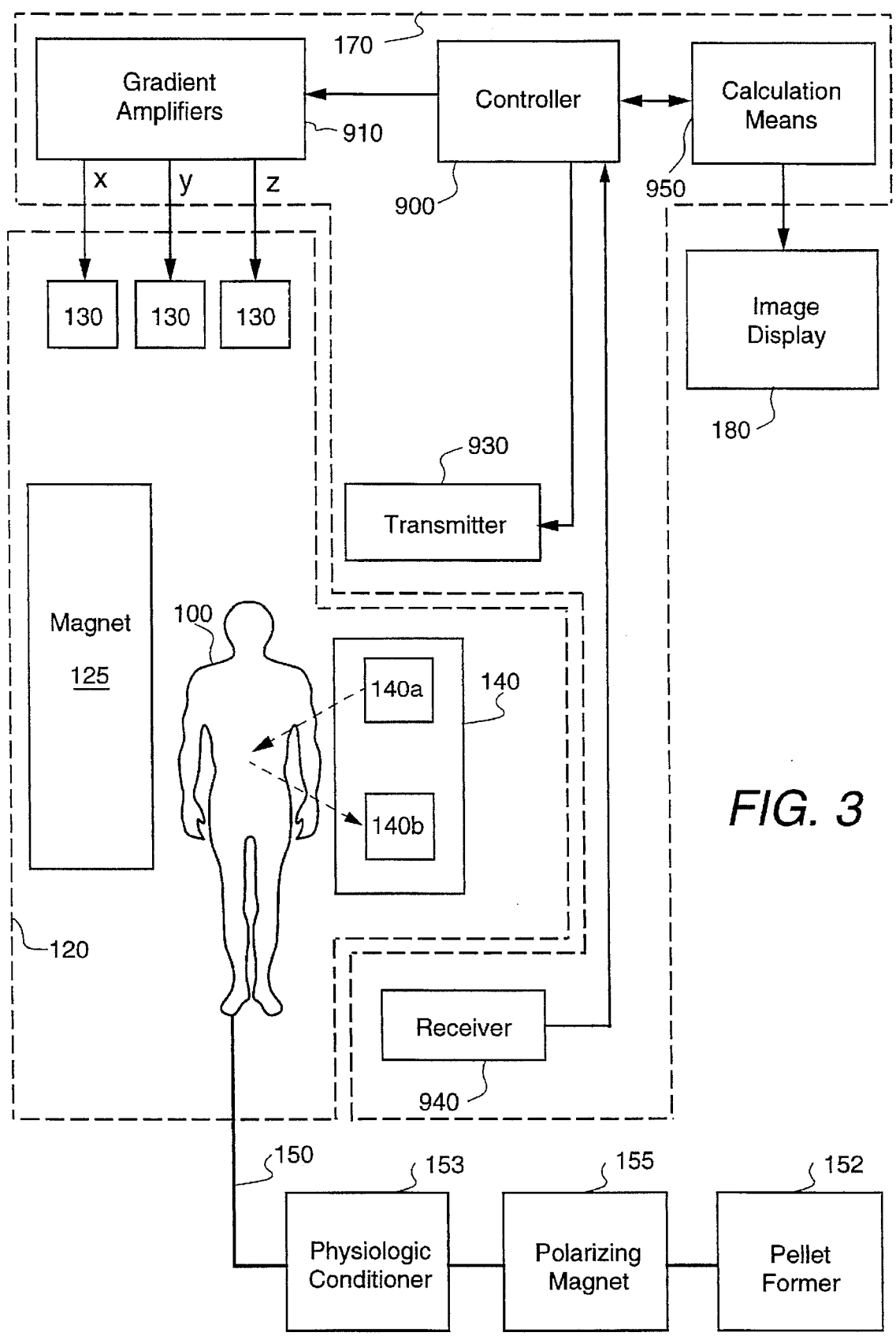
FIG. 3 is a simplified block diagram of a vessel selective MR imaging system suitable for MR angiography according to the present invention.

RF transmitter 930 and RF receiver 940 of the MR system shown in FIG. 3 would be compatible with the low-field magnet to operate at a Larmor frequency corresponding to the strength of magnet 125 (e.g., 4.26 MHz in a 0.1 Tesla magnetic field).

In an alternate embodiment, imaging magnet 125 could be an electromagnet which is driven by an amplifier similar to amplifier 910. Such a system should be able to create a pulsed homogeneous field of typically 30 Gauss (Larmor frequency=128 kHz). Shielded gradient coil designs meant to reduce the undesirable effects of eddy currents induced in the magnet structure by pulsed gradient fields may be unnecessary with the present invention employing a low-field main magnet 125 (although such designs may still be desirable to prevent interference with nearby equipment).

A controller 900 provides control signals to magnetic field gradient amplifiers 910. These amplifiers drive magnetic field gradient coils 130 situated within the magnet enclosure 120. Gradient coils 130 are capable of generating magnetic field gradients in three mutually orthogonal directions.

Controller 900 generates signals which are supplied to a transmitter 930 to generate RF pulses at one or more predetermined frequencies and with suitable power to nutate selected spins within RF coil 140 situated within the bore of magnet 125. Separate RF transmit 140a and receive 140b coils may be employed instead of a single RF transmit and receive coil 140.

Transmitter 930, and RF coil 140 of the present invention perform the same functions as an RF subsystem of a conventional MR imaging device. If the Larmor frequency is very low, RF coil designs having resonant frequencies comparable to the Larmor frequency will be required. At these lower frequencies, very little RF transmit power will be required, being a further advantage of the present invention.

MR response signals are sensed by RF coil 140 connected to receiver 940. Since the fluid being injected into subject 100 has passed through polarizing magnet 155, it acquires a significantly larger longitudinal magnetization, $M_L$, than material which has only been subjected to low-field magnet 125. Consequently, when nutated by the RF pulses, 'spins' which have passed through polarizing magnet 155 exhibit larger transverse magnetization, $M_L$, and consequently produce a much larger MR response signal. Receiver 940 processes the MR response signals by amplifying, demodulating, filtering and digitizing. Controller 900 also collects the signals from receiver 940 and propagates them to a calculation means 950 where they are processed. Calculation means 950 applies a Fourier transformation to the signals received from controller 900 to create an MR image. The image created by calculation means 950 is displayed on an image display tneans 180.

The signal-to-noise ratio and contrast of signals from subject 100 can be estimated for an embodiment of the present invention in which a 0.1 Tesla imaging magnet is used with a 10.0 Tesla polarizing magnet and a cryogenic pellet former operating at 4 degrees Kelvin. The MR response signal of 'spins' in subject 100 which did not pass through polarizing magnet 155 experience a 0.1 T magnetic field. Spins that pass through the 10T polarizing magnet, however, will have a polarization which is 100 times stronger. Pellets polarized at 4 degrees Kelvin have an additional factor of 66.5 in polarization. Therefore, the MR signal difference, or contrast, between polarized and non-polarized 'spins' would be a hctor of 6,650. Note that in a conventional imaging system which does not use any enhanced polarization means, the ratio of signal intensity in the blood vessels and surrounding tissue is approximately 1 and rarely greater than 2.

The MR system outlined in FIG. 3 may also be used for the generation of conventional MR images in a manner well known to those skilled in the art. Received MR response signals are detected with either the same RF coil used by the transmitter or a surface coil independent of the coil driven by the transmitter.

While several presently preferred embodiments of the novel MR vascular imaging system have been described in detail herein, many modifications and variations will now become apparent to those skilled in the art. It is, therefore, to be understood that the appended claims are intended to cover all such modifications and variations as fall within the true spirit of the invention.

What is claimed is:

1. A magnetic resonance (MR) imaging system for obtaining vessel-selective MR angiographic images from a subject comprising:
   a) an imaging magnet for applying a substantially uniform magnetic field over said subject;
   b) a cryogenic pellet-forming means for freezing a portion of a selected fluid to form pellets;
   c) a high-field polarizing magnet having a cavity for receiving and polarizing the pellets;
   d) a physiologic conditioner means for heating the polarized pellets into a polarized contrast fluid of a temperature suitable for injection into said subject;
   e) an invasive device for routing the polarized contrast fluid from the physiologic conditioner means into said subject;
   f) an RF transmitter means for transmitting RF energy into said subject of a selected duration, amplitude and frequency to cause nutation of the contrast fluid and other tissue within said subject;
   g) a gradient means for varying the amplitude of the magnetic field in at least one spatial dimension over time;
   h) an RF receive coil for detecting a set of MR response signals from the contrast fluid and other tissue within said subject;
   i) a receiver means coupled to the RF receive coil for receiving the detected MR response signals;
   j) a calculation means for calculating an image from the detected MR response signals;
   k) a controller means connected to the RF transmitter means, the receiver means, the calculation means and the gradient means, for activating the RF transmitter means, the receiver means, the calculation means and the gradient means each according to a predetermined MR pulse sequence; and
   l) a display means connected to the calculation means for displaying the calculated image to an operator.

2. The magnetic resonance (MR) imaging system of claim 1 further comprising a mechanical device for transferring the pellets from the cryogenic pellet-forming means to the physiological conditioner means.

3. The magnetic resonance (MR) imaging system of claim 1 wherein the high-field polarizing magnet has a cylindrical shape and is constructed to maximizes its magnetic field intensity produced in its cavity without regard to homogeneity of the magnetic field within its cavity.

4. The magnetic resonance (MR) imaging system of claim 1 wherein the high-field polarizing magnet has a size which is substantially smaller than an MR imaging magnet which surrounds the entire subject.

5. The magnetic resonance imaging system as described in claim 1 wherein the polarizing magnet produces a stronger magnetic field than the imaging magnet.

6. A method of obtaining magnetic resonance (MR) angiographic images from a subject comprising:
   a) applying a substantially homogeneous magnetic field over said subject;
   b) cooling a contrast fluid to form a solid;
   c) polarizing the solid by passing it through a high-field polarizing magnet;
   d) heating the polarized solid to obtain a polarized contrast fluid;
   e) routing the polarized contrast fluid into a selected vessel of said subject;
   f) transmitting RF energy into said subject of a selected duration, amplitude and frequency to cause nutation of the contrast fluid and other tissue within said subject;
   g) varying the amplitude of the magnetic field in at least one spatial dimension over time;
   h) detecting a set of MR response signals from the polarized contrast fluid and other tissue within said subject;
   i) receiving the detected MR response signals;
   j) calculating an image from the detected set of MR response signals; and
   k) displaying the calculated image to an operator.

7. The method of obtaining magnetic resonance (MR) angiography images of claim 6 wherein the contrast fluid is passed through the polarizing magnet in the absence of a radiofrequency (RF) excitation pulse.

* * * * *